United States Patent [19]

Eisenbeis

[11] Patent Number: 5,795,718
[45] Date of Patent: Aug. 18, 1998

[54] DETECTION OF COMPLEMENTARY NUCLEOTIDE SEQUENCES

[75] Inventor: Scott J. Eisenbeis, Benicia, Calif.

[73] Assignee: Boehringer Mannheim Corporation, Indianapolis, Ind.

[21] Appl. No.: 453,971

[22] Filed: May 30, 1995

Related U.S. Application Data

[63] Continuation of Ser. No. 745,153, Aug. 15, 1991, abandoned.
[51] Int. Cl.$^6$ .......................... C07H 21/04; C07H 21/00; C07H 19/04
[52] U.S. Cl. .......................... 435/6; 536/22.1; 536/24.3; 536/25.32; 536/26.6
[58] Field of Search .......................... 435/6; 536/24.3, 536/22.1, 25.32, 26.6

[56] References Cited

U.S. PATENT DOCUMENTS

| | | | |
|---|---|---|---|
| 4,708,929 | 11/1987 | Henderson | 435/7 |
| 4,775,619 | 10/1988 | Urdea | 435/6 |
| 4,868,103 | 9/1989 | Stavrianopoulos et al. | 435/5 |

FOREIGN PATENT DOCUMENTS

| | | | |
|---|---|---|---|
| 0 144 913 | 6/1985 | European Pat. Off. | |
| 0144914 | 6/1985 | European Pat. Off. | 435/6 |
| 0 0164 054 | 12/1985 | European Pat. Off. | |
| 0 151 001 | 12/1985 | European Pat. Off. | |
| 0 419 081 A2 | 3/1991 | European Pat. Off. | |
| 0419081 | 3/1991 | European Pat. Off. | 435/6 |

WO 90/13569 11/1990 WIPO.

OTHER PUBLICATIONS

Clin. Chem., vol. 32, No. 9, pp. 1637–1964 Henderson et al. (1986).

*Primary Examiner*—Kenneth R. Horlick
*Assistant Examiner*—Joyce Tung
*Attorney, Agent, or Firm*—Morrison & Foerster, LLP

[57] ABSTRACT

The invention relates to a method for detection of a specific nucleic acid sequence which comprises forming a reaction mixture by combining (1) a sample suspected of containing a nucleic acid;

(2) a probe/enzyme donor polypeptide conjugate comprising
   (a) an enzyme donor polypeptide sequence comprising a β-galactosidase fragment; and
   (b) a single-stranded oligonucleotide sequence attached to (a) and capable of hybridizing with said nucleic acid;

(3) an enzyme acceptor polypeptide capable of forming an active enzyme upon complementation with said enzyme donor fragment; and (4) a substrate for β-galactosidase; and detecting hybridization of said probe/enzyme donor conjugate to said sample nucleic acid to form a double strand-specific sequence by determining the amount or rate of enzyme activity on said substrate in said reaction mixture. The method can also include a "proof reading" function by incubating the hybridized probe with at least one double-strand-specific, sequence-specific restriction endonuclease.

Novel kits for use in carrying out the method are also included.

24 Claims, 4 Drawing Sheets

5' H2N--GAG GAT CCC CGG GTA CCG AGC TCG 3'
     BamHI   SmaI  KpnI  SacI

5'...TGATTACGAATTCGAGCTCGGTACCCGGGGATCCTCTAGAGTCGA...3'
         EcoRI  SacI  KpnI  SmaI  BamHI  XbaI lacI' lacZ'
M13 72506

DETECTION OF COMPLEMENTARY NUCLEOTIDE SEQUENCES

CROSS REFERENCE TO RELATED APPLICATIONS

This application is a continuation of U.S. application Ser. No. 07/745,153, filed Aug. 15, 1991, now abandoned.

TECHNICAL FIELD

The invention relates to a method for detection of specific complementary sequences in nucleic acids, and to new kits for use in such methods.

BACKGROUND OF THE INVENTION

Nucleic acid hybridization represents an extremely powerful method for the detection and identification of genetic material. Hybridization is the formation of a double-stranded nucleic acid from single-stranded molecules when the base sequences in the strands are complementary. Hydrogen bonds hold the complimentary strands together and make the double-stranded complex very stable.

However, hybridization between two single stranded nucleic acids is dependent upon the complementarity of the two sequences. This is the principle behind the extreme specificity possible when using nucleic acid hybridization as an analytical tool. Radioactive or enzyme labeling of a nucleic acid has made it possible to monitor the formation of sequence specific hybridization events and therefore detect the presence of nucleic acid sequence of medical interest.

"Target" nucleic acids from the genomes of protozoa, bacteria, molds, fungi, viroids, and viruses or any other plant or animal life form can be detected and identified using labeled single-stranded nucleic acid "probes". In addition to infectious agents, DNA probe methodologies can be used to analyze human DNA to determine if abnormalities in DNA sequence are present which are associated with the occurrence of genetic disease. These assays not only must detect the presence of a specific DNA sequence but also subtle changes in the sequence resulting from point, insertion, or deletion mutations. Interest in specific sequences may involve the determination of the presence of alleles, the presence of lesions in a host genome, the detection of a particular mRNA or the monitoring of a modification of a cellular host.

Cystic fibrosis, thalassemia, sickle cell anemia, and Huntington's disease are a few examples of the genetic diseases detectable using probe hybridization. However the techniques currently used to detect the presence of infectious agents or abnormalities in a human DNA sample are cumbersome and time consuming.

The most widely used procedure is known as the Southern blot filter hybridization (Southern, E. J., *Mol. Biol.* 98: 503, (1975). This method is widely used for detection of infectious agents and genetic disease. The DNA from an appropriate sample is cleaved with restriction endonucleases and the resulting fragments are electrophoretically separated on an acrylamide or agarose gel. The fragments are then transferred to a nitrocellulose sheet which immobilizes the cleaved target DNA. The sheet is then incubated with denatured, labeled probe. During this incubation, sequence specific hybridization takes place. Bands which are indicative of the presence of an infectious agent or a genetic disease can be visualized by autoradiography of the nitrocellulose sheet after excess labeled probed is washed away. Although this method is very sensitive and accurate in detecting specific nucleic acid sequences, it requires a considerable amount of technical expertise to perform. In addition it is very time consuming, requires specialized equipment and utilizes radioactivity as a label.

U.S. Pat. No. 4,358,535 reveals a method for detection of an infectious agent by the hybridization of its nucleic acid to a radiolabeled probe. The method involves extraction of genetic material from a clinical sample which is fixed to a solid support in a single-stranded form. The immobilized nucleic acid is then incubated with radiolabeled, single-stranded nucleic acid which is complementary to the nucleic acid of the pathogen of interest. If the target nucleic acid is present in the sample, the radiolabeled probe can be detected on the solid phase after unhybridized probe is washed away. This method also suffers from the undesirability of working with radioactivity. In addition, it is impractical when working with large numbers of samples to immobilize the nucleic acid from each sample on solid phase.

European Patent Application No. 0117,440 discloses a similar methodology except non-radioactive chemically-labeled probe is used. European Patent Application No. 0070,685 describes a homogeneous hybridization system that utilizes a non-radioactive energy transfer system for detection. This system requires two probe strands which hybridize adjacent to each other on the target DNA. The first probe carries a chemiluminescent catalyst while the second has an absorber emitter moiety. When the two probes are brought into close proximity, light emitted is measured by an appropriate instrument and indicates the presence of target nucleic acid. Other relevant disclosures include U.S. Pat. No. 4,486,539, a "sandwich" probe assay; Langer, et al., *Proc. Natl. Acad. Sci. USA* (1981) 78: 6633, the use of avidin-biotin for nucleic acid affinity probes; and U.S. Pat. No. 4,868,104, use of probe-covered beads in conjunction with a secondary probe which results in increased bead diameter in the presence of target.

As can be seen from the above discussion, the current ability to detect a specific nucleic acid or a subtle change in a nucleic acid are limited by one or more of the following factors, cost, time, skill, instrumentation, safety, sensitivity and background signal.

Methods for the detection of specific nucleotide sequences employing a solid support, at least one label, and hybridization involving a sample and a labeled probe, where the presence or absence of duplex formation results in the ability to modify the spatial relationship between the support and label(s) are disclosed in U.S. Pat. No. 4,775,619.

U.S. Pat. No. 4,868,105 describes methods and compositions for detecting particular nucleic acid sequences involving two reagents where the first reagent results in labelling the analyte sequence and the second reagent provides the means for separating label bound to analyte from unbound label in the assay medium. Conventional techniques are employed to detect the presence or absence of the label.

The above patents which describe various techniques of hybridization requiring the binding of a polynucleotide sequence to a support and employing a labeled probe are incorporated herein by reference.

An ideal detection system would be inexpensive, homogeneous, calorimetric, simple, and applicable to pathogenic or non-pathogenic agents as well as genetic targets. It would avoid the use of hazardous radioactivity and provide a sensitive and accurate system for detecting specific nucleic acid sequences.

BRIEF DESCRIPTION OF THE FIGURES

The invention can be more fully understood by reference to the following detailed description of the invention, and to the appended drawings in which.

SUMMARY OF THE INVENTION

The invention provides for methods and compositions for the detection of specific target nucleic acid sequences.

The invention provides the ability to detect the presence or absence of a nucleic acid of specific sequence and also provides the ability to detect subtle differences in nucleic acid sequences. These abilities are directly useful for the detection and identification of pathogenic and non-pathogenic conditions and genetic traits, including the presence or absence of a gene in plant or animal cells, (a) without requiring growth of the cells to a stage at which phenotype is expressed and/or (b) when the gene is recessive.

In specific embodiments, the invention utilizes a probe which is a conjugate of a single- stranded DNA oligonucleotide and a polypeptide fragment (ED) which represent a portion of the sequence of β-galactosidase. This ED polypeptide is capable of reassociating with specific inactive β-galactosidase deletion mutant proteins (a process known as enzyme complementation) to form an active β-galactosidase. The rate of reassociation of the two inactive β-galactosidase fragments is modulated by hybridization of target nucleic acid to the probe/ED conjugate.

Additional methods are provided which use a restriction endonuclease to verify the formation of a sequence specific hybrid between the target and the probe/ED conjugate. Methods are also described which utilize the above methods and compositions to discriminate between subtle differences in nucleic acid.

DETAILED DESCRIPTION OF THE INVENTION

The invention is directed to a method for detection of a specific nucleic acid sequence (target) in a sample which comprises forming a reaction mixture by combining
(1) a sample;
(2) a nucleic acid probe/enzyme donor polypeptide conjugate comprising
 (a) an enzyme donor polypeptide sequence comprising a β-galactosidase fragment; and
 (b) a single-stranded oligonucleotide cross-linked to (a);
(3) an enzyme acceptor polypeptide, wherein said enzyme acceptor polypeptide is capable of forming an active β-galactosidase enzyme upon complementation with said enzyme donor polypeptide fragment; and
(4) a substrate for β-galactosidase; and determining the amount of said substrate that reacts with active β-galactosidase.

The ability of the hybridized probe/enzyme donor conjugate to combine with the enzyme acceptor is affected by the additional steric and coulombic contribution of the hybridized nucleic acid from the sample. Hybridization of the probe/enzyme donor conjugate to the sample nucleic acid to form a double strand-specific sequence can be detected by determining the amount of enzyme activity on the substrate in the reaction mixture.

Figure 4:
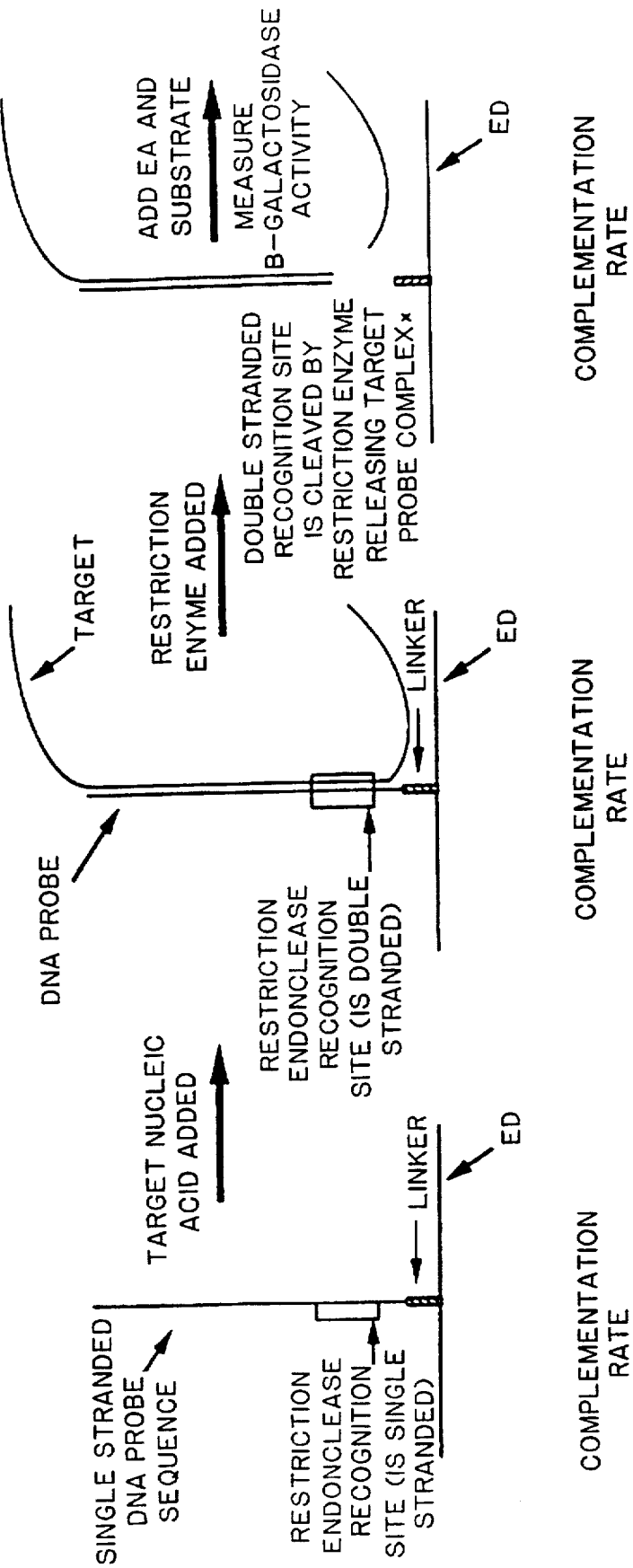
FIG. 4 diagrammatically represents the steps which take place during one of the preferred embodiments of the invention. Panel A depicts the ED/probe reagent which is a conjugated single-stranded nucleic acid to an ED. A site for specific restriction endonuclease is positioned adjacent to the point of conjugation. Panel B depicts hybridization between the single-stranded probe and the target nucleic acid which is either single-stranded by nature or made single-stranded previous to this step. Panel C depicts cleavage of the double-stranded nucleic acid hybrid by the double-strand specific restriction endonuclease. The complementation activity observed in Panels B and C are lower and higher respectively, than the activity observed in Panel A.

The present invention can be used for a probe assay according to FIG. 4, Panels A and B, or without a nuclease as given in Panel C of FIG. 4. This is applicable to all combinations of probe assays where both target or probe could be either RNA or DNA. When the probe is RNA and the target is DNA, RNase H can be used in the place of a restriction endonuclease in Panel C of FIG. 4. RNase H specifically degrades the RNA strand of an RNA-DNA hybrid. This would have the effect of removing the probe from the ED only if the nucleic acid target is present.

The invention is based upon complementation of the enzyme β-galactosidase. A number of patent applications and patents relating to the complementation assays and visually detectable methods for use therein have arisen out of the laboratories of the present inventors. Those patents and applications that are directed to β-galactosidase enzyme donors and acceptors are U.S. Pat. No. 4,708,929; U.S. application Ser. No. 788,370, now U.S. Pat. No. 5,128,653, filed Oct. 22, 1985 now U.S. Pat. No. 5,120,153; U.S. application, Ser. No. 347,675, filed May 5, 1989 abandoned; U.S. application, Ser. No. 410,996, filed Sep. 22, 1989 now abandoned; and PCT application, PCT/US 90/02491, filed May 4, 1990, as an international PCT application designating the U.S.. All of these patents and patent applications are herein incorporated by reference.

As described in the above disclosures, the β-galactosidase complementation system has allowed sensitive immunoassays and receptor assays to be developed for analytes of a wide range of molecular weights. The assays are based on a complementation of β-galactosidase. "Complementation" refers to the spontaneous reassembly of two individually inactive fragments of β-galactosidase protein which combine to form a fully active β-galactosidase enzyme. The smaller of the two inactive polypeptides in a complementation is referred to as an "α donor" (hereinafter also referred to as "enzyme donor" or "ED") and the larger as an "α acceptor" (hereinafter also referred to as "enzyme acceptor" or "EA"). The enzyme donor consists approximately of the N-terminal $\frac{1}{10}$–$\frac{1}{20}$ of the β-galactosidase amino acid sequence. The enzyme acceptor represents approximately the remainder of the sequence of β-galactosidase.

These polypeptide components of β-galactosidase can be utilized to construct a homogeneous, colorimetric, nucleic acid "probe" assay for the detection of nucleic acid of specific sequence. This is accomplished by chemically attaching a single-stranded nucleic acid sequence to the enzyme donor polypeptide fragment. This single-stranded nucleic acid sequence (herein also referred to as the "probe") is complementary or substantially complementary to the sequence of the nucleic acid whose detection is desired (herein also referred to as the "target") in a sample.

The techniques for the hybridization of DNA are disclosed in many references, including Walker and Gaastra (eds.) *Techniques in Molecular Biology* (1983) MacMillan Publishing Company, New York, pp 113–135 and 273–283; Maniatis et al., (eds) *Molecular Cloning* (1982) Cold Spring Harbor Laboratory, pp 309; E. Southern, *J. Mol. Biol.* (1875) 98: 503: Botchan et al., *Cell* (1976) 9: 269; Jeffreys et al., *Cell* (1977) 12: 429. These disclosures are incorporated herein by reference.

The single-stranded nucleic acid can be prepared by known techniques for making and isolating probe oligonucleotide sequences, including automated internucleotide synthesis. For example, Sigma Chemical Company "Biochemical Organic Compounds for Research and Diagnostic Reagents" (1990) and *Science*, 251: 251 (Mar. 8, 1991) describe commercially available probes and reagents for use in (automated) oligonucleotide synthesis.

Such probe sequences bear chemical linking functional groups at the 5' end, which permit coupling with various other reagents. The introduction of such linking groups is carried out by various procedures known in the art, including U.S. patent application Ser. No. 537,905, filed Jun. 12, 1990 now U.S. Pat. No. 5,223,393. When the linking functional group is a polymeric material, various procedures are known in the art for the activation of polymer surfaces and the attachment of immunoglobulins, glycoproteins, saccharide-containing organic molecules, and polynucleotides. See U.S. Pat. Nos. 4,419,444; 4,775,619; 3,956,219; and 3,860,386 as well as European Patent Application No. 84308143.1 and Scouten, W. H. (ed.) *Solid Phase Biochemistry, Analytical and Synthetic Aspects* (1983), Wiley & Sons, New York, page 779.

The length of the probe sequence will depend on the nature of the target and can readily be determined by those of skill in the art. By way of non-limiting example, the probe sequence comprises from about 15 nucleotides to about 100 nucleotides, preferably from about 20 nucleotides to about 45 nucleotides.

The group conjugating the linking functional group of the nucleic acid probe sequence and linking functional group of the ED can be merely a bond, for example, where an acid group can be activated to react with the amino group of ED, or can be any bifunctional material of one or more atoms usually from about 1 to 24 atoms, more usually from about 1 to 12 atoms and especially about 1 to 6 carbon atoms and 0 to 6, preferably 0 to 4 heteroatoms. Besides carbon atoms, heteroatoms in the chain can include nitrogen, sulfur, oxygen or the like, wherein oxygen is present as oxy or oxo, nitrogen is present as amino or amido and sulfur is present as thio or thiono. Examples of such groups which are well known in protein chemistry, include dialdehydes such as glutaraldehyde and diamines such as 1,6-diaminohexane. Other suitable linking materials include organic polymers, both naturally occurring and synthetic, such as polysaccharides, styrene polymers, polyacrylates, e.g., polyacrylamide, hydroxyethyl polymethacrylates, glass, ceramic, carbon, polyvinyl chloride, protein, and the like. Styrene polymers include polystyrene, polymers containing aromatic moieties and higher aromatic compounds such as naphthalene, anthracene, etc. Covalent bonding is preferred.

Any of the known specific binding pairs can also be used to conjugate the nucleic acid probe sequence to the ED. For example, the biotin-avidin binding pair can be used wherein one member is attached to the probe and one to the ED. Antigen-antibody interaction could also be used as a linking system. For example, the small molecule dinitrophenol (DNP) and anti-DNP antibody.

A large number of linking functional groups on the nucleic acid probe sequence and on the ED can be employed in conjugating or linking a wide variety of specific single-stranded nucleic acid sequences to the ED. For the most part, the functional group present in the ED for linking will be a mercaptan or amino group. For linking mercaptan groups of the ED, of particular interest are a wide variety of readily available reagents, involving activated halogen, activated olefin, or mercapto, where the first two form thioethers and the second a disulfide. Specific linking agents include N-maleimidobenzoic acid, α-bromoacetamidocyclohexane-carboxylic acid, N-maleimidosuccinic acid, methyldithio-acetic acid, and the like. For linking amino groups of the probe or ED, a wide variety of active halogens or carboxylic acid groups can be employed, particularly activated carboxylic acid groups, where the carboxylic acid groups can be activated with carbodiimide, active esters, such as N-hydroxy succinimide, o-nitrophenol, p-nitrophenol, and the like. For linking the phosphoric acid functional group of the probe, activating groups can be used, such as imidazolide. The procedures for conjugation are well known in the literature and are amply illustrated by U.S. Pat. Nos. 3,817, 837; 4,262,089; 4,233,401; 4,220,722 and 4,374,925. One preferred linking agent is succinimidyl-1-4-(N-maleimidomethyl) cyclohexane-1-carboxylate (SMCC).

The ED and EA fragments for use in the invention are well known in the art and include those described in assignee's U.S. Pat. Nos. 4,708,929 and 4,956,274, the disclosures of each of which are incorporated herein by reference. Since the ED and EA fragments are well known, there is need for only a brief description of the ED and EA fragments. This technology is useful with all of the ED and EA variants described in U.S. Pat. No. 4,708,929. In addition, this technology is applicable to 'Omega complementation' which is described in co-pending U.S. patent application Ser. No. 07/700,549 filed on May 15, 1991, now abandoned and whose disclosure is herein incorporated by reference.

The ED sequence will usually be from about $\frac{1}{10}$ to about $\frac{1}{20}$ of the total amino acid sequence of β-galactosidase, usually from about 60 to about 100 amino acids. The ED sequence will generally be modified or mutated to provide for the presence of a cysteine or a lysine unit, which introduces a mercapto or amino functional group for use in preparing an ED conjugate of the invention.

The methods of preparing an EA are well known and can include isolation from a naturally occurring mutant source, or the EA can be synthesized using known recombinant techniques.

When the probe/donor conjugate is incubated with single-stranded nucleic acid target, the probe and target will hybridize (anneal) to form a double-stranded segment of nucleic acid where the probe and target sequences are complementary. The ability of hybridized probe/donor conjugate to reassociate with acceptor is negatively impacted by the additional steric and coulombic contribution of the bound target. This effect on complementation can easily be seen by monitoring the complementation activity of the probe/donor conjugate with and without bound target. This reduction of complementation activity is reflected as a decrease in β-galactosidase activity.

An additional step can be added after the hybridization of target and probe. This step involves the addition of a double strand-specific, sequence-specific restriction endonuclease (herein also referred to as "restriction endonuclease"). The utilization of this step includes choosing a probe sequence having at least one restriction endonuclease site adjacent to the point of linkage to the polypeptide enzyme donor.

The term "double-strand-specific, sequence-specific restriction endonuclease" as used herein is a site specific endodeoxyribonuclease and isoschizomers thereof. In general, the chemical structure of these materials has not been established but about one hundred of these materials have been identified and their use and reactions are carried out empirically.

In the present invention any hybridized probe is now present in the form of double-stranded nucleic acid and as such is contacted (incubated) with the double-strand-specific, sequence-specific restriction endonuclease to release the hybridized probe.

Because the probe/donor conjugate carries a single-stranded nucleic acid sequence, the unhybridized probe is not cleaved by restriction endonuclease. However, when the probe and target hybridize, they form a double-stranded recognition site, which is cleaved by the restriction endonuclease. The result is that the target and the probe are released from the donor peptide. The result of this release is an increase in the enzyme complementation rate. The rate, is higher than the complementation rate of the target-probe/donor complex and in fact is higher than the complementation rate of the probe/donor itself. The reason for this is that not only is target released by restriction endonuclease cleavage, but the conjugated probe is also released. The removal of the steric and coulombic effects of the hybridized probe allows the enzyme donor to complement the enzyme acceptor more efficiently.

The restriction endonuclease cleavage serves to verify the formation of a double-stranded hybrid. In addition, because of the sequence specificity of restriction endonucleases, this second step provides a powerful "proof reading" function. The restriction endonuclease will only cut if the substrate is double-stranded and only if the correct sequence is present in the recognition site. If a single base does not match the recognition site, the enzyme will not cut. This quality allows the present invention to discriminate between two target sequences in which the only difference is a single base change.

The importance of this ability is apparent when the present invention is applied to the detection of genetic disease. For example, sickle cell anemia is caused by a single base change that corresponds to the sixth amino acid in β-globin (GAG4GTG). This mutation also destroys a recognition site for the restriction endonuclease Mst II. The present invention can be used to discriminate between normal and sickle cell β-globin DNA sequences by designing a probe sequence which is exactly complimentary to the normal β-globin sequence and subsequently cutting the hybridized probe with Mst II or one of its isoschizomers. If the probe is hybridized to a normal sequence target, it will be cleaved by Mst II but if it is hybridized to sickle cell sequence target, it will not be cleaved.

Therefore, despite the fact that a single base mismatch is not sufficient to prevent hybridization to probe (except under very carefully controlled conditions), the single base change can still be detected by using the sequence-specificity of restriction endonucleases. The present invention would also similarly be useful to discriminate between closely related infectious agents.

The present invention is also uniquely able to exploit the ability of some nucleic acid amplification systems (see U.S. Pat. Nos. 4,683,202 and 4,683,195, European Patents 272, 098 and 224,126 and PCT Patent Application 87/3,451) to incorporate new, allele-specific restriction endonuclease sites into the amplified target (Friedmann, et al., *Clin. Chem.* 36: 695; Haliassos, et al., *Nucleic Acids Res.* 17: 3606). Other amplification systems which are relevant include the NASBA amplification system (*Nature*, 350: 91), the TAS amplification system (*Proc. Natl. Acad. Sci. U.S.A.*, 86: 1173), and the 3SR amplification system (*Proc. Natl. Acad. Sci. U.S.A.*, 87: 1873).

These amplification systems allow normal and mutant sequences to be differentiated by cleaving the amplified target with the appropriate restriction endonuclease and electrophoretically separating the fragments. However, the present invention can be used to differentiate between normal and mutant amplified products in a homogeneous, calorimetric format, as described above.

The assay method is usually conducted in an assay medium comprising the reagents in a suitable buffer. The buffer formulation is not critical. In general, any physiologically acceptable buffer can be used including phosphate buffered saline, Tris buffer and the like. In one embodiment of the invention, the buffer comprises from about 100 mM to about 300 mM of sodium phosphate, or about 300 mM to about 500 mM of sodium chloride, about 5 mM to about 15 mM of EGTA or EDTA, and about 5 mM to about 20 mM of sodium azide having a pH of between about 6 to about 8.

A chelating agent can be added to any polypeptide fragments containing cysteine residues to protect against metal-catalyzed oxidation. Addition of a stabilizing amount of a chelating agent for metal ions, such as EDTA, ethylenediamine tetraacetic acid, or EGTA, ethylene glycol tetraacetic acid, is desirable.

A bactericide, such as sodium azide, can be present to prevent bacterial growth, especially during storage.

Other materials can be present including but not limited to magnesium ions or other ions for enzyme activity, reagents to prevent degradation of cysteine residues such as dithiothrietol (DTT), solubilizing agents such as ethylene glycol, and non-ionic surfactants, such as fatty acid condensation products of sorbitol and ethylene oxide (e.g., Tween 20) and the like. Methionine and bovine serum albumin (BSA) can also be present.

The storage stable assay medium is typically aqueous. The ED fragment is usually present at a concentration from about 2 pM to about 5 nM, and EA is present in varying degrees of excess.

The sample can be obtained from any source of interest such as microorganisms, bacteria, viruses, viroids and plant and animal life forms, including physiological fluids, such as blood, serum, plasma, spinal fluid, vitreous humor, and the like. Where the sample is double-stranded nucleic acid, it will be necessary to treat the sample to denature the double-stranded molecules before mixing with the ED-probe conjugate. Denaturation can be achieved most readily by subjecting the sample to high temperature. Other means for denaturation can be utilized such as treating the sample with alkaline solutions or concentrated solutions of formamide or through use of other procedures known in the art. The sample can be subjected to prior treatment, including sample preparations described in U.S. Pat. No. 4,556,643, or be used as obtained.

The amount of sample that can be used in conjunction with the present invention depends, among other things, upon the concentration of the analyte, the nature of the sample, and the sensitivity of the assay.

After combining the various reagents of the assay medium and the sample to form a reaction mixture, the assay medium will usually be incubated for at least about 0.2 min and usually not more than about 15 min, preferably from about 1 min to about 10 min. The temperature of the incubation will usually be within the temperature range compatible with nucleic acid hybridization reactions, for example, from about 40° C. to about 100° C. The mixture is then removed from elevated temperature and is incubated with or without a sequence specific restriction endonuclease. The incubation conditions are determined by the individual enzyme. The preferable length of the incubation would be less than 15 minutes. EA and substrate are then added and complementation activity is measured. The assay method of the invention is generally and preferably performed at atmospheric pressure. The time required for hybridization or conjugation depends on the concentration and sequence complexity of the nucleic acid probe, as well as on the assay temperature, solvent, and reagent concentrations and the like.

An enzyme substrate is used in the method of the invention that when cleaved by β-galactosidase results in a detectable change in the amount of light absorbance (optical density) or emission. That is, cleavage of the substrate results in the appearance or disappearance of a color, chemiluminescent or fluorescent product suitable for spectrophotometric, chemical or fluorometric analysis. Substrate suitable for use with β-galactosidase include but are not limited to p-aminophenyl-p-β-galactopyranoside, 2'-N-(hexadecanol)-N-(amino-4'-nitrophenyl)-β-D-galactopyanoside, 4-methylumbelliferyl-β-D-galactopyranoside, naphthyl-A-S-B1-β-D-galactopyranoside, 1-naphthyl-β-D-galactopyanoside, 2-naphthyl-β-D-galactopyranoside monohydrate, o-nitrophenyl-β-D-galactopyranoside, m-nitrophenyl-β-D-galactopyranoside, p-nitrophenyl-β-D-galactopyranoside, phenyl-β-D-galactopyranoside, 5-bromo-4-chloro-3-indolyl-β-D-galactopyranoside, resorufin-β-D-galactopyranoside, 7-hydroxy-4-trifluoromethylcoumarin, omega-nitrostyryl-β-D-galactopyranoside, fluorescein-β-D-galactopyranoside, chlorophenol red galactoside and the like. Preferred substrates are chlorophenol red galactoside (CGRP) and o-nitrophenyl-β-D-galactoside (ONPG). Incubation with the enzyme substrate results in cleavage of the substrate to produce a product that is detectable, preferably by color.

In a further embodiment, the invention also provides a kit for facilitating the assay method. The kit comprising (1) a probe/enzyme donor polypeptide conjugate for detecting a specific nucleic acid sequence comprising a conjugate of (a) an enzyme donor polypeptide sequence comprising a β-galactosidase fragment;

(b) a single-stranded oligonucleotide; and (c) a linking group connecting said enzyme donor to said single-stranded oligonucleotide; and (2) an enzyme acceptor polypeptide capable of forming an active enzyme upon complementation with the enzyme donor fragment, in at least one container.

The kit can further comprise substrate and at least one restriction endonuclease in separate containers. The details and preference previously expressed above with regards to the novel probe and method also apply to the kit.

Unless specified otherwise above, the relative amounts of reagents used in the invention can vary widely to provide for concentrations of the reagents which can substantially optimize the sensitivity of the assay method. The reagents can be provided as dry powders, usually lyophilized, including any excipients, which on dissolution will provide for a reagent solution having the appropriate concentration for performing the assay method of the invention.

Materials and Definitions used in the examples below include:

SMCC: succinimidyl-1,4-(N-maleimidomethyl)-cyclohexane carboxylate, a heterobifunctional linking agent.

ONPG: o-nitrophenyl-β-galactoside (substrate).

ED4: the coding for ED4 is set forth in Section 5.1.6 of U.S. Pat. No. 4,708,929.

Figures 2, 3:
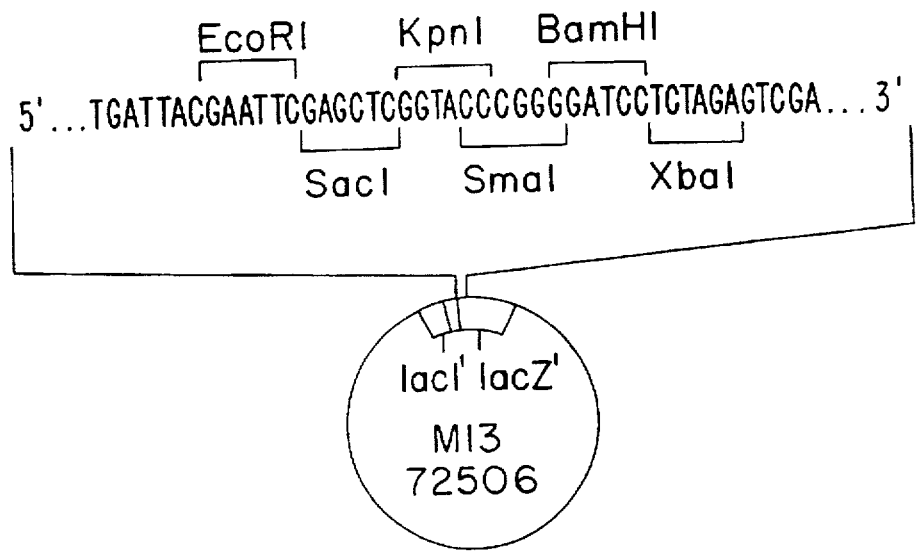
FIG. 2 represents a single-stranded DNA sequence of a probe, BP-1, for M13 mp18. The probe contains restriction endonuclease sites for Bam HI, Sma I, Kpn I and Sac I. A primary amine linker at the 5' end of the sequence facilitates its conjugation to the ED peptide. This sequence has SEQ ID NO:1.
FIG. 3 represents the target nucleic acid M13 mp18. The sequence of the viral genome which is complementary to the probe BP-1 is also shown. This sequence has SEQ ID NO:2.

BP-1: SEQ ID NO:1 as set forth in FIG. 2.

M13 mp18: SEQ ID NO:2 as set forth in FIG. 3.

$T_{20}$: a homooligonucleotide of twenty thymine residues.

CPRG: chlorophenol red galactoside (substrate).

EGTA: ethylene glycol tetraacetic acid.

Tween 20: a trade name designating polyoxyethylenesorbitan, a condensation product of an ether of polyoxyethylene and sorbitol with dodecanoic acid and other fatty acids including lauric acid approximately 50% and a balance of myristic, palmitic, and stearic acids.

EA22: enzyme acceptor complementary to ED4 is set forth in Section 5.2 of U.S. Pat. No. 4,708,929.

TEAA: triethylammonium acetate.

Buffer for digestion of T20 by Nuclease $P_1$
 20 mM sodium acetate
 4 mM magnesium acetate
 pH 5.3

Buffer for EA, ED and substrate
 150 mM sodium phosphate
 400 mM sodium chloride
 10 MM EGTA
 0.05% Tween 20
 10 mM Methionine
 5 mg/ml bovine serum albumin
 pH=7.0
 3 mM $MgCl_2$

EXAMPLE 1

Preparation of ED-Nucleic Acid Conjugates

Oligonucleotides were chemically synthesized using phosphoramidite chemistry on a Applied Biosystems 380B DNA synthesizer. During the final cycle of each synthesis a linker group of either 3 or 6 carbons, and terminating in a primary amine, was introduced to the 5' end of the completed nucleotide sequence. The products were deprotected, ethanol precipitated and used without further purification. Two oligonucleotides were synthesized in this way. The first was a homooligonucleotide of twenty thymine residues ($T_{20}$) and the second was a oligonucleotide 24 bases long (BP-1, SEQ ID NO:1) containing sites for the restriction endonucleases Bam HI, Sma I, Kpn I and Sac I. To facilitate the conjugation of the nucleic acid to the ED peptide, both oligonucleotides were derivatized at the primary amine of the linker group. The heterobifunctional linking agent, succinimidyl-1,4-(N-maleimidomethyl) cyclohexane-1-carboxylate (SMCC), was added in 10-fold molar excess and reacted for 40 minutes at room temperature. Because only full length oligonucleotide chains carry the amine linker, shorter length failed sequences do not react with SMCC and are easily separated by HPLC. The products of SMCC derivitization were purified from the starting materials by HPLC on a C-4 reverse-phase column using an acetonitrile gradient (10–30%, $T_{20}$; 9–14%, BP-1, whose sequence is set forth in SEQ ID NO:1) in triethylammonium acetate (TEAA) pH 7.0. The pooled products were concentrated by lyophilization and later redissolved in sodium phosphate buffer 100 mM, pH 7.0. Two-fold excess of ED-4 containing a single cysteine sulfhydryl was added to each derivatized oligonucleotide. The reaction was carried out for 20 min at room temperature. The final conjugation products were purified by reverse phase HPLC using an acetonitrile gradient (20–35%, ED4-$T_{20}$; 24–31%, ED4-BP-1) in TEAA buffer pH 7.0. Concentration of the ED-nucleic acid conjugates were assigned using the calculated extinction coefficients of ED4-$T_{20}$ and ED4-BP-1.

Complementation Activity of ED4-$T_{20}$

In order to determine the relative complementation activity of ED4-$T_{20}$ compared to a standard ED-analyte conjugate, ED-4 digoxigenin, both ED4-digoxigenin and ED4-$T_{20}$ were complemented with EA22 (hereafter "EA") and resulting enzyme activity measured. ED4-digoxigenin was titrated ($4.25\times10^{-10}$–$4.25\times10^{-9}$ mol) and the complementation activity measured after EA and ONPG substrate addition, as mAU/min at 420 nm. The complementation rate of a fixed amount of ED4-$T_{20}$ ($4.25\times10^{-9}$ mol) was similarly measured. The rate of product formation was compared to the standard curve produced from the ED4-digoxigenin titration. The results showed that ED4-$T_{20}$ complements 24% as efficiently as ED4-digoxigenin under the experimental conditions.

Recovery of Complementation Activity By Nuclease Treatment of ED4-$T_{20}$

Figure 1:
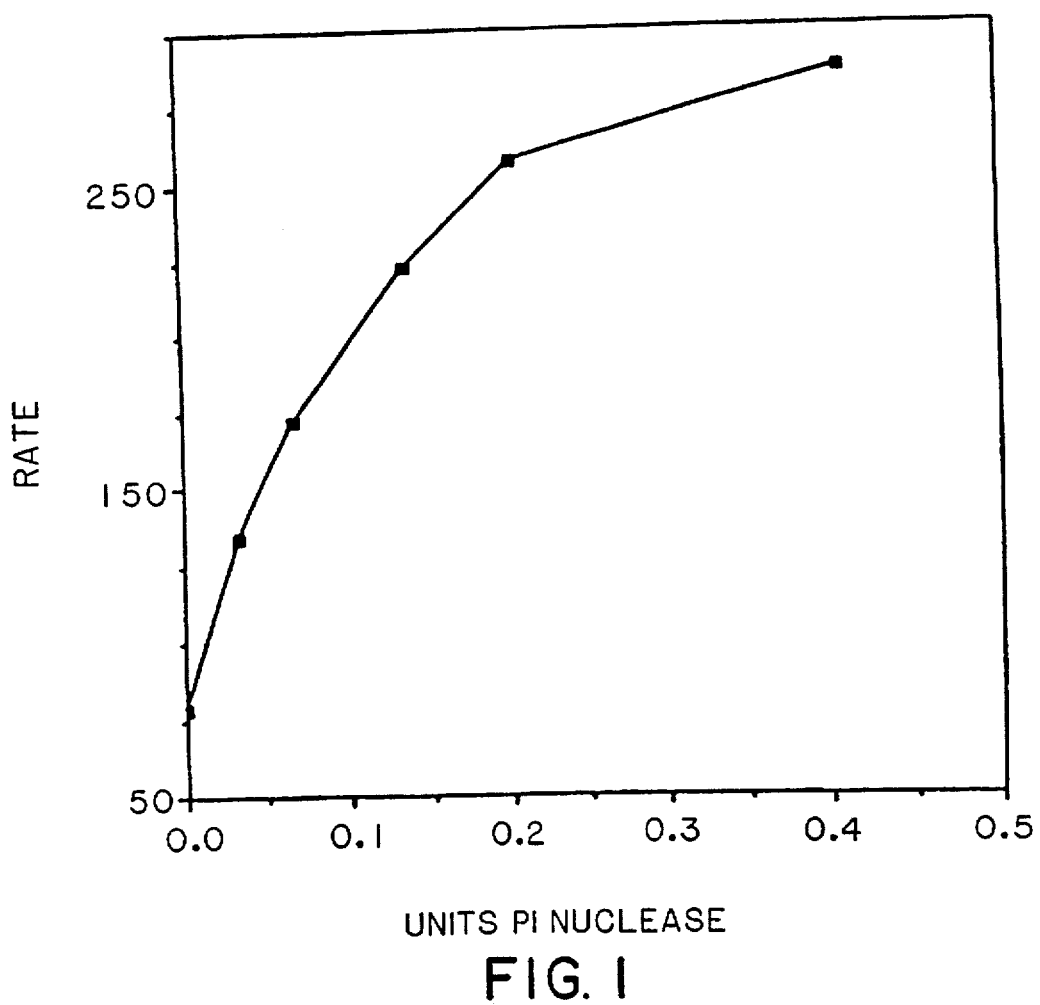
FIG. 1 graphically represents the time-course digestion of $T_{20}$ from an $ED_4$-$T_{20}$ conjugate by nuclease P1. This model system demonstrates that the complementation activity of an ED-nucleic acid conjugate increases as the nucleic acid is enzymatically removed.

In order to show that full complementation activity of ED4 could be regained by removal of the $T_{20}$ oligonucleotide, an automated assay was developed on a COBAS BIO clinical analyzer to monitor complementation activity after digestion with various amounts of nuclease. ED4-$T_{20}$ was incubated at 37° C. for 16.5 minutes with various amounts of nuclease, P1 (Bethesda Research Laboratories), in 20 mM Na acetate pH 5.3, 4 mM Mg acetate. At the end of the incubation period, EA and the substrate, CPRG, were added in 150 mM Na phosphate, pH 7.2, 400 mM NaCl, 10 mM EGTA, 0.05% Tween 20 and 10 mM methionine. The rate of product formation was measured at 574 nm in mAU/min. The results (FIG. 1) indicate that the complementation activity of ED4-$T_{20}$ can be increased by digestion of the conjugate with nuclease. An almost 5-fold increase in activity is seen between the use of no nuclease and highest concentration restriction endonuclease conditions.

EXAMPLE 2

Recovery of Complementation Activity By Nuclease Treatment of ED4-BP-1

ED4-BP-1 was subjected to nuclease, P1, treatment as described for ED4-$T_{20}$. However, only the highest amount of nuclease was used to digest ED4-BP-1 to ensure complete removal of the nucleic acid strand. The complementation rates of the digested and undigested ED4-BP-1 were 467.93 and 183.54 mAU/min, respectively. Therefore roughly a 2.5 x increase is observed by removal of the nucleic acid.

EXAMPLE 3

Complementation Activity of ED4-$T_{20}$ After Hybridization with A$_{300}$

ED4-$T_{20}$ was hybridized with a polyadenylate chain with an average length of 300 residues (A$_{300}$, Sigma). Complementation activity of the resulting ED4-$T_{20}$:A$_{300}$ complex was compared to that of the unhybridized ED4-$T_{20}$. ED4-$T_{20}$ ($4.25\times10^{-9}$ mol) was incubated with or without A$_{300}$ ($5\times10^{-8}$ mol) in 60 mM K phosphate pH 7.0, NaCl 400 mM, EGTA 10 mM, 0.05% Tween 20, 3mM MgCl$_2$ and 10 mM Na azide (bactericide) for 5 minutes at room temperature. EA and ONPG were then added and the rate of change in absorbance was measured at 420 nm after 3 minutes of incubation at 30° or 37° C.

The results demonstrated that A$_{300}$ inhibited complementation when hybridized to ED4-$T_{20}$. The degree of inhibition is temperature dependent as the Tm of the hybridized complex is approximately 40° C. Complementation was inhibited 43% at 37° C., compared to unhybridized ED4-$T_{20}$, and inhibited 60% at 30° C. The presence of A$_{300}$ does not affect the complementation of ED4 not conjugated with $T_{20}$.

EXAMPLE 4

Complementation Activity of ED4-BP-1 Before and After Hybridization To Target Nucleic Acid In order to determine whether an ED-nucleic acid conjugate would be useful as a probe for the complementation activity detection of specific nucleic acid sequences, a conjugate was made of ED4 and BP-1. BP-1 is a single-stranded DNA oligonucleotide 24 bases long (SEQ ID NO:1, FIG. 2). The BP-1 sequence is complementary to the multiple cloning site region of the single-stranded DNA from the bacteriophage M13 mp18 (SEQ ID NO:2, FIG. 3). The viral DNA which is about 7250 bases in length was used as a model target nucleic acid. $2.4\times10^{-10}$ mol of ED4-BP-1 conjugate was incubated with and without $2.4\times10^{-9}$ mol of M13 mp18 DNA at 55° C. for 10 minutes. EA (20 U/test) and CPRG (2.0 mg/ml final) were then added and the mixture incubated at 37° C. for 4 minutes. The rate of increase in A$_{574}$ was measured per minute between 4 and 6 minutes. The rates of complementation were 80.73 and 47.16 mAU/min without and with target M13 DNA mp18 DNA, respectively. Therefore complementation was reduced approximately 42% (FIG. 4) by hybridization with the target nucleic acid.

EXAMPLE 5

Effect of Addition of Sequence-Specific Restriction Endonuclease to a Target-Bound ED4-BP-1 Conjugate When single-stranded target M13 (SEQ ID NO:2) and probe BP-1 (SEQ ID NO:1) sequences hybridized they formed a double-stranded stretch of 24 bases. Contained in the double-stranded sequence were the recognition sequences for the restriction endonucleases Bam HI, Sma I, Kpn I and Sac I.

Figure 5:
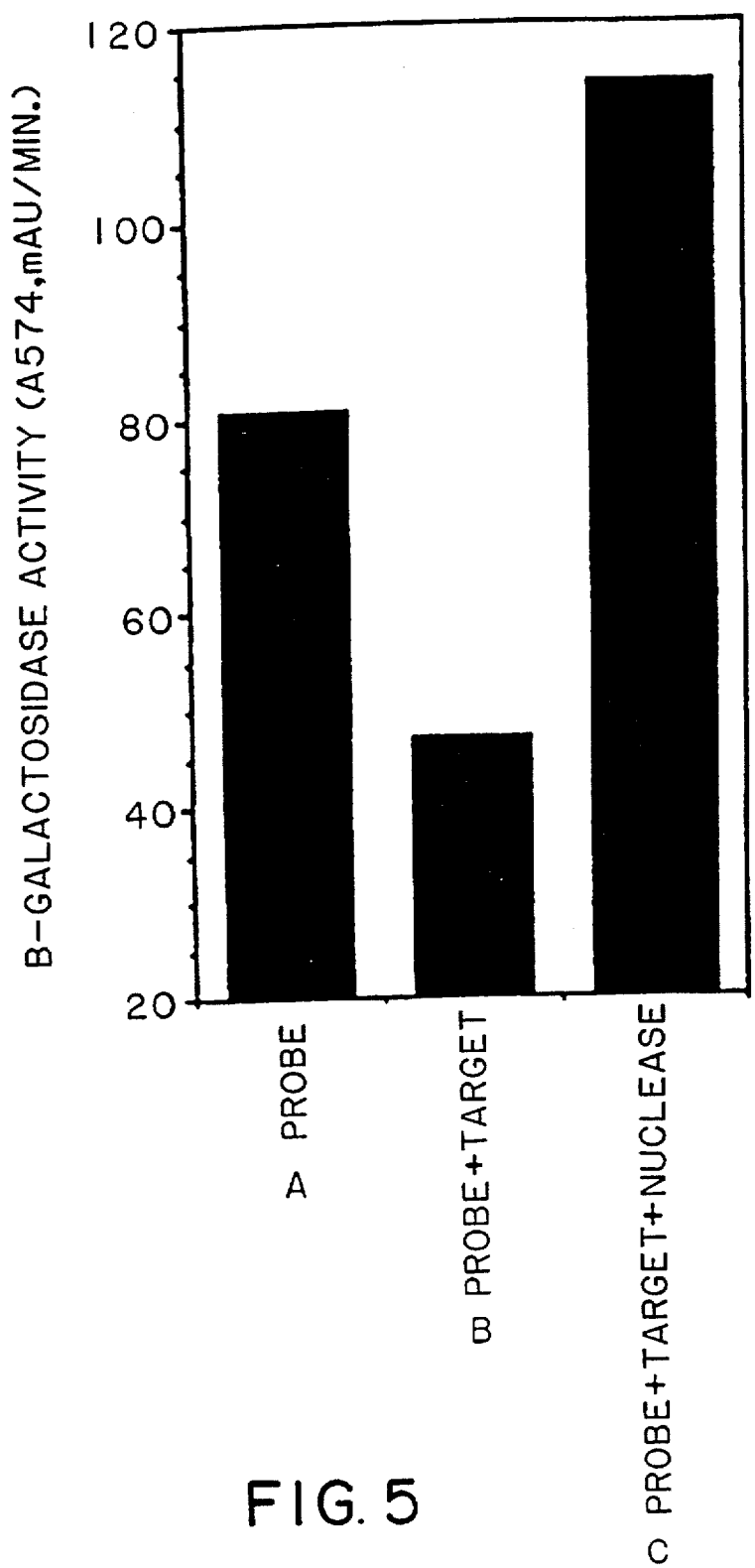
FIG. 5 graphically represents the complementation activity of the $ED_4$-BP-1 conjugate at the three stages described in FIG. 4; (a) the $ED_4$-BP- 1 conjugate alone, (b) the conjugate hybridized to target nucleic acid, and (c) the ED-probe conjugate and target hybrid after cleavage by the restriction endonuclease Bam HI.

ED4-BP-1 was hybridized to M13 mp18 for 10 min at 55° C. The hybridized complex was then incubated both with and without Bam HI at 37° C. for 40'. Cleavage of the ED4-BPI/M13 mp18 complex with Bam HI released the target DNA completely and the probe DNA except for 2 bases. The complementation efficiency of the ED4-BP-1/M13 mp18 complex before and after digestion with Bam HI was measured. The rate of increase in A574 was measured per minute as described above. The rates were 47.16 and 114.07 for samples without and with Bam HI added, respectively. Cleavage of the probe/target hybrid in this model system therefore, increased the rate of complementation approximately 2.4 fold (FIG. 5).

EXAMPLE 6

Specificity of the Effect of M13 Target Binding and Bam HI Cleavage

In order to test the specificity of the probe/target interaction and of the Bam HI cleavage, several control experiments were carried out. ED4-BP-1 and ED4-T$_{20}$ were incubated with and without Bam HI.

No difference in enzyme complementation rate was observed whether or not Bam HI was added. Therefore, Bam HI was specific for cleavage of the probe/target complex and does not cleave single-stranded probe DNA under the experimental conditions.

ED4-T$_{20}$ was incubated with and without M13 mp18 target DNA for 15 minutes at 37° C. and then assayed as described above for enzyme complementation activity. No difference was seen in samples, with or without M13 DNA. This demonstrated that the specificity of hybridization between probe and target is necessary to inhibit complementation.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for detection of a nucleic acid sequence in a sample which comprises the steps of:
(A) combining, either sequentially or concurrently,
  (1) a sample suspected of containing a nucleic acid of interest;
  (2) a probe/enzyme donor conjugate consisting essentially of
    (a) an enzyme donor comprising a β-galactosidase fragment 1/10–1/20% of the length of the N-terminal β-galactosidase amino acid sequence, which forms active β-galactosidase upon complementation with an enzyme acceptor polypeptide; and
    (b) a single-stranded oligonucleotide sequence attached to (a) using a conjugating group and which can hybridize with said nucleic acid;
  (3) an enzyme acceptor polypeptide consisting essentially of a fragment of β-galactosidase, wherein said enzyme acceptor polypeptide forms said active β-galactosidase enzyme upon complementation with said probe/enzyme donor conjugate; and
  (4) a substrate for β-galactosidase; and
(B) detecting hybridizing between said nucleic acid and said oligonucleotide sequence to form a hybridized sequence by determining the amount or rate of enzyme activity.

---

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( v i ) ORIGINAL SOURCE:
        ( A ) ORGANISM: bacteriophage ( i x ) FEATURE:
        ( A ) NAME/KEY: CDS
        ( B ) LOCATION: 1...24

( x i ) SEQUENCE DESCRIPTION: SEQ ID NO:1:

GAG GAT CCC CGG GTA CCG AGC TCG    24

( 2 ) INFORMATION FOR SEQ ID NO:2:

( i ) SEQUENCE CHARACTERISTICS:
        ( A ) LENGTH: 45 nucleic acids
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

TGA TTA CGA ATT CGA GCT CGG TAC    24

CCG GGG ATC CTC TAG AGT CGA    45

2. The method of claim 1 wherein said oligonucleotide sequence includes at least one restriction endonuclease recognition site, and wherein said detecting step includes contacting a double-strand-specific restriction endonuclease specific for said restriction endonuclease recognition with said hybridized sequence prior to determining the amount or rate of enzyme activity.

3. The method of claim 2 wherein said restriction endonuclease recognition site is proximal to the point of attachment of the single-stranded oligonucleotide sequence to the enzyme donor.

4. The method of claim 2, wherein the amount of enzyme activity on said substrate is determined by detection of the amount of light absorbance or emission.

5. The method of claim 2, wherein said detection is of a visually detectable signal.

6. The method of claim 2, wherein said detection is of a fluorescent or chemiluminescent signal.

7. The method of claim 2, wherein said sample nucleic acid is amplified prior to said combining.

8. The method of claim 7, wherein said sample nucleic acid is amplified using polymerase chain reaction or β-replicase.

9. The method of claim 1 wherein said sample nucleic acid is RNA.

10. The method of claim 1, wherein said sample nucleic acid is DNA.

11. The method of claim 1, wherein said oligonucleotide sequence includes at least one restriction endonuclease recognition site, and wherein said detecting step includes contacting a double-strand-specific restriction endonuclease specific for said restriction endonuclease recognition with said hybridized sequence after initially determining the amount or rate of enzyme activity in the absence of said restriction endonuclease.

12. A probe/enzyme donor polypeptide conjugate for detecting a target nucleic acid sequence comprising:
  (a) an enzyme donor polypeptide comprising an enzyme donor fragment that forms an active enzyme upon complementation with an enzyme acceptor polypeptide; and
  (b) a single-stranded oligonucleotide capable of hybridizing with said target nucleic acid sequence said single stranded oligonucleotide attached to the enzyme donor polypeptide.

13. The probe/enzyme donor polypeptide conjugate of claim 12 in combination with an enzyme acceptor polypeptide that is capable of forming an active enzyme upon complementation with the enzyme donor polypeptide.

14. The probe/enzyme donor polypeptide conjugate of claim 12, in combination with an enzyme acceptor polypeptide that is capable of forming an active enzyme upon complementation with the enzyme donor polypeptide in further combination with at least one double-strand-specific restriction endonuclease.

15. The probe/enzyme donor polypeptide conjugate of claim 12 wherein the enzyme donor comprises a fragment of a hydrolytic enzyme.

16. The probe/enzyme donor polypeptide conjugate of claim 15 wherein the hydrolytic enzyme is β-galactosidase.

17. The probe/enzyme donor polypeptide conjugate of claim 16 wherein the enzyme donor fragment consists essentially of an N-terminal $1/10$–$1/20$ β-galactosidase fragment.

18. A method for detection of a nucleic acid sequence in a sample which comprises the steps of:
  (A) combining, either sequentially or concurrently,
    (1) a sample suspected of containing a nucleic acid of interest;
    (2) a probe/enzyme donor conjugate consisting essentially of
      (a) an enzyme donor fragment that forms an active enzyme upon complementation with an enzyme acceptor polypeptide; and
      (b) a single-stranded oligonucleotide sequence capable of hybridizing with said nucleic acid said single stranded oligonucleotide attached to said enzyme donor fragment;
    (3) an enzyme acceptor polypeptide consisting essentially of an enzyme fragment, wherein said enzyme acceptor polypeptide forms active enzyme upon complementation with said probe/enzyme donor conjugate; and
    (4) a substrate for the enzyme; and
  (B) detecting hybridizing between said nucleic acid and said oligonucleotide sequence by determining the amount or rate of enzyme activity.

19. The method of claim 18 wherein the enzyme donor fragment and the enzyme acceptor polypeptide are fragments of a hydrolytic enzyme.

20. The method of claim 19 wherein the hydrolytic enzyme is β-galactosidase.

21. The method of claim 20 wherein the enzyme donor fragment consists essentially of an N-terminal $1/10$–$1/20$ β-galactosidase fragment.

22. A kit comprising:
  (1) a probe/enzyme donor polypeptide conjugate for detecting a specific nucleic acid sequence consisting essentially of an N-terminal $1/10$–$1/20$ conjugate of
    (a) an enzyme donor comprising a β-galactosidase fragment that forms an active β-galactosidase upon complementation with an enzyme acceptor polypeptide; and
    (b) a single-stranded oligonucleotide sequence attached to (a) using a conjugating group and which can hybridize with said nucleic acid;
  (2) an enzyme acceptor polypeptide capable of forming an active β-galactosidase enzyme upon complementation with (a); in at least one container and
  (3) at least one double-strand-specific restriction endonuclease in a separate container.

23. The kit of claim 22, wherein said kit additionally comprises in a separate container enzyme substrate solution that optionally contains said enzyme acceptor polypeptide.

24. The kit of claim 22, wherein more than one restriction endonuclease is present.

* * * * *

UNITED STATES PATENT AND TRADEMARK OFFICE

CERTIFICATE OF CORRECTION

PATENT NO.: 5,795,718
DATED : August 18, 1998
INVENTOR: Scott J. Eisenbeis

It is certified that error appears in the above-identified patent and that said Letters Patent is hereby corrected as shown below:

Column 14, line 10: In claim 1.(A)(2)(a), after --1/10-1/20-- please delete "%"

Column 16, lines 39-45: In claim 22, please delete the text of sections (1) and (1)(a), beginning with "(1) a probe/enzyme donor polypeptide" to and including "tide; and" and replace with the following:

--(1)a probe/enzyme donor polypeptide conjugate for detecting a specific nucleic acid sequence comprising a conjugate of
    (a)    an enzyme donor consisting essentially of an N-terminal 1/10-1/20 β-galactosidase fragment that forms an active β-galactosidase upon complementation with an enzyme acceptor polypeptide; and--

Signed and Sealed this

Seventh Day of September, 1999

*Attest:*

Q. TODD DICKINSON

*Attesting Officer*       *Acting Commissioner of Patents and Trademarks*